(12) United States Patent
Nardotto

(10) Patent No.: US 6,344,113 B1
(45) Date of Patent: Feb. 5, 2002

(54) METHOD AND DEVICE FOR GENERAL AND LOCALIZED SANITIZING OF AIR AND SIMILAR GAS MIXTURES

(76) Inventor: Giannantonio Nardotto, Via Ten. Pivato, 6, 36063 Marostica (Vicenza) (IT)

( * ) Notice: Subject to any disclaimer, the term of this patent is extended or adjusted under 35 U.S.C. 154(b) by 0 days.

(21) Appl. No.: 09/565,152

(22) Filed: May 5, 2000

(30) Foreign Application Priority Data

May 7, 1999 (IT) .......................................... VI99A0088
Apr. 21, 2000 (IT) .......................................... VI20A0073

(51) Int. Cl.[7] .............................. H05F 3/00; B01J 19/08
(52) U.S. Cl. .................................. 204/164; 422/186.04
(58) Field of Search .................... 422/186.04; 204/164; 55/105, 126

(56) References Cited

U.S. PATENT DOCUMENTS

| | | | | |
|---|---|---|---|---|
| 4,376,642 A | * | 3/1983 | Verity | 55/105 |
| 4,597,781 A | * | 7/1986 | Spector | 55/126 |
| 5,435,837 A | * | 7/1995 | Lewis et al. | 96/54 |
| 5,529,613 A | * | 6/1996 | Yavnieli | 96/63 |
| 5,549,735 A | * | 8/1996 | Coppom | 96/63 |
| 5,942,017 A | * | 8/1999 | Van Winkle, Sr. | 55/385.1 |

* cited by examiner

*Primary Examiner*—Kathryn Gorgos
*Assistant Examiner*—Thao Tran
(74) *Attorney, Agent, or Firm*—R. Neil Sudol; Henry Coleman; William Sapone

(57) ABSTRACT

A method for the general and localized sanitizing of air and similar gas mixtures, to be applied in aeraulic climate-control systems of buildings and in the preparation and preservation of perishables, the method including a continuous and constant or intermittent negative ionization of the air of an environment, so as to have a bactericidal and microbicidal action on the air without producing ozone and to have a neutralizing action on toxic gaseous compounds such as benzene, $NO_x$ and the like or an action which converts the toxic compounds into non-toxic compounds.

14 Claims, 3 Drawing Sheets

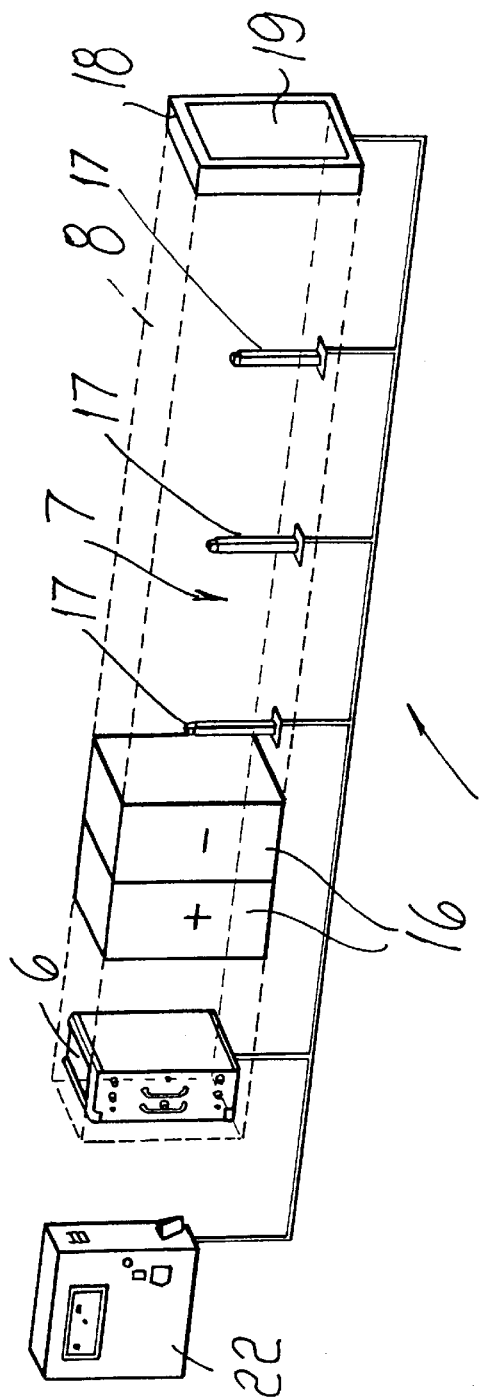
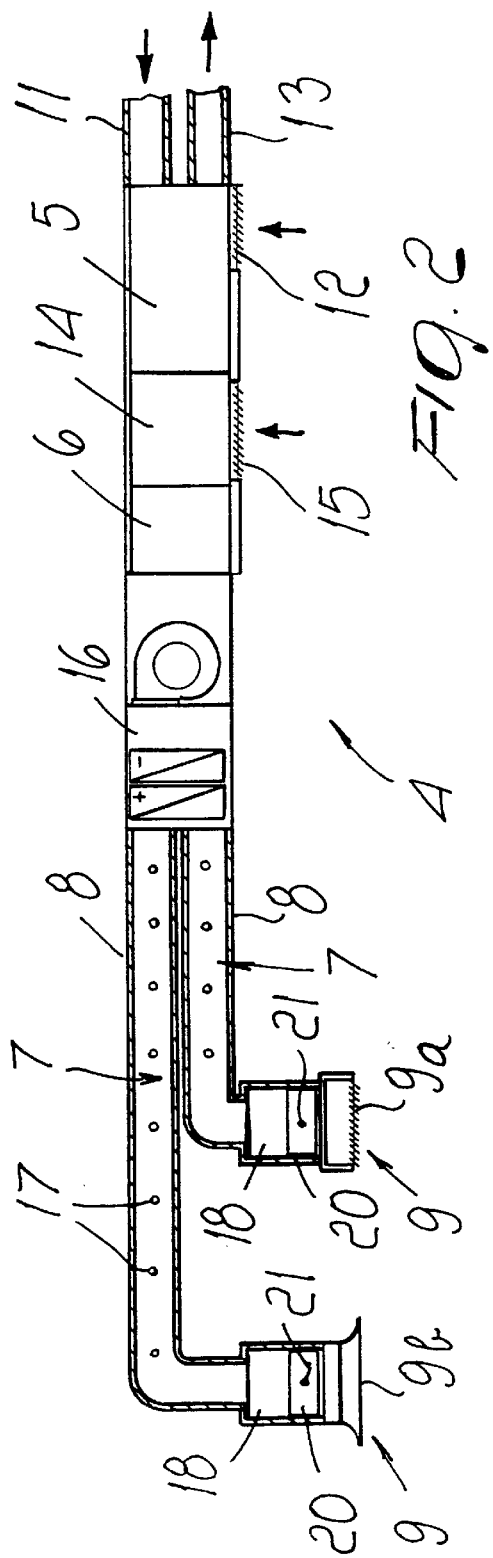

METHOD AND DEVICE FOR GENERAL AND LOCALIZED SANITIZING OF AIR AND SIMILAR GAS MIXTURES

BACKGROUND OF THE INVENTION

1. Field of the invention

The present invention relates to a method and a device for general and localized sanitizing of air and similar gas mixtures, particularly but not exclusively to be applied in aeraulic and climate-control systems of hospitals, business centers, offices and rooms in general, in the preparation and preservation of perishables, and for neutralizing or converting toxic gaseous compounds such as benzene, $NO_x$ and the like into non-toxic gaseous compounds.

2. Description of the Prior Art

Most modern buildings are equipped with sophisticated systems which maintain appropriate comfortable environmental conditions inside the buildings. In this context, the characteristics closely linked to the chemical composition of air, such as low bacterial activity, absence of pollution, et cetera, have become very important over the last decade because it has been found experimentally that conventional systems often cause the onset of certain diseases. Unless scrupulous maintenance of the system, consisting in effectively cleaning and disinfecting the surfaces that are in direct contact with the air, is performed at regular intervals, the system and particularly its ducts, filters et cetera become the ideal medium for the proliferation of viruses, molds and bacterial colonies such as the feared Legionella pneumophila and Bacillus cereus. On the other hand, the maintenance of installed systems is a very significant burden, since it mainly depends on the extent of the network of ducts, which can be very large in multistory buildings such as hospitals, shopping centers, et cetera. The adoption of electrostatic precipitation filters partially solves the problem of eliminating bacterial colonies by trapping dust, since it is well-known that many bacteria are conveyed in free air by dust, preferably on particles having a diameter of a few microns. It is also known that the organic decay of food products and the like is a natural and inevitable phenomenon triggered by bacteria and microbes conveyed everywhere by air and present in the air. This process of decay begins on the exposed surface that is in direct contact with the surrounding environment and then progresses inward until the component organic substances are completely deteriorated. The macroscopic effects of this phenomenon consist of the appearance of surface mold and a change in the odor and color of the food product. The main microscopic effects consist of the gradual loss of the organoleptic properties of the food product, which accordingly entails the decay of the nutritional properties thereof and their consequent toxicity. It is also known that the bacteria and microbes that are present in the air are active in every step of the production process of food for human beings and animals. At present, technology essentially offers an "external" method of intervention and an "internal" method for delaying this process of decay. The "external" method consists of preservation at temperatures below 0° C. until freezing is achieved, which physically paralyzes the noxious action of bacteria and microbes. The "internal" method consists in adding substances, known as preservatives, which chemically inhibit this action. Very often, these methods are combined appropriately so as to further extend their effects. The main drawback of the "external" method is the high energy expenditure required to achieve prolonged preservation at such temperatures. In turn, the main drawback of the "internal" method is the fact that the preservatives may, in the long term, turn out to be noxious for the human body. Experimental research has shown that ionized air has a strong bactericidal effect. For example, the researchers Philips, Harris and Jones, by nebulizing a large quantity of bacteria in an enclosed space and subjecting them to ionization, have found that the mortality rate of the bacterial load is 54% with positively ionized air and 78% with negatively ionized air. A further confirmation of this phenomenon is provided by the experience of the researcher Lautie, who ionized the air in an enclosed space with a volume of 120 $m^3$ and with an approximate concentration of 83,000 bacteria per cubic meter of air, noting that this concentration dropped rapidly and became zero in approximately three quarters of an hour. Further confirmation is provided by the researchers Kellog and Fratini, who carried out tests and measurements on Staphilococcus aureus and on molds, respectively. These experimental findings are explained by the fact that ionization of the air leads to the breakdown of the bonds of oxygen molecules such as $O_2$ and therefore produces free oxygen $O^-$, which in the gaseous state, being an oxidizing agent, has a bactericidal and microbicidal action.

SUMMARY OF THE INVENTION

The aim of the present invention is to overcome the drawbacks noted above, providing a method and a device for the general and localized sanitizing of air and similar gas mixtures which give the treated air high-level characteristics of purity both in terms of particulate and in bacteriological and microbial terms.

An object of the invention is to provide a method and a device which allow to prevent and eliminate the forming of molds and bacterial colonies along air distribution ducts and to effectively prolong the preservation of perishable products.

Another object of the invention is to provide a method and a device which allow a substantial reduction of maintenance interventions over time and specifically of interventions for cleaning along the ducts, extending their life, and to achieve this prolonged preservation, even in combination with known methods, at lower costs and in a more natural manner without producing ozone.

Another object of the invention is to provide a device which is preferably constituted by connectable modular units, so as to contain production costs, installation costs, maintenance costs and component replacement costs, and which is applied in many different fields in the sector of perishable product preparation and preservation.

This aim, these objects and others which will become apparent hereinafter are achieved by a method for the general and localized sanitizing of air and similar gas mixtures, as claimed in the accompanying claims.

BRIEF DESCRIPTION OF THE DRAWINGS

Further characteristics and advantages of the invention will become apparent from the description of a preferred but not exclusive embodiment, illustrated only by way of non-limitative example in the accompanying drawings, wherein:

FIG. 1 is a schematic perspective view of an example of a device for general sanitizing according to the invention;

FIG. 2 is a detailed view of the device of FIG. 1;

DESCRIPTION OF THE PREFERRED EMBODIMENTS OF THE INVENTION

The method for the general and localized sanitizing of air and similar gas mixtures, according to the invention, comprises an initial step in which air to be sanitized is aspirated continuously. The air is constituted by air recycled from the enclosed space into which the sanitized air is released and by external air, preferably with a 70/30 ratio, in order to ensure correct re-oxygenation of the enclosed space and at the same time contain energy consumption by limiting air changes as much as possible. In particular cases it is possible to perform the method exclusively with recycled or external air. The air thus aspirated is subjected to a step of intensive dust collection in two stages, respectively by virtue of a prefiltering and by electrostatic precipitation, so as to trap most of the dust and with it any microbes, fumes, et cetera. Then the dust-free air is treated in order to give it temperature and humidity characteristics suitable for the conditions required in the enclosed space into which it will be released. Said air is then subjected to ionization, which sterilizes the bacteria and microbes that have survived the dust collection step. Conveniently, the ionizing field is negative, so as to reinforce the bactericidal and microbicidal action, and for the same reason the concentration of negative ions introduced in the dust-free air is very high and constant over time or intermittent. Generally speaking, the concentration is at least two orders of magnitude higher than the concentration that is normally present in free air, i.e., approximately 400–1200 ions per cubic centimeter. After this passage, the excess ions, which accordingly have not contributed to the sterilization process, are neutralized in order to reestablish the electrostatic balance in the dust-free air. At this point the air is sanitized and released into the enclosed space. During this last step the air is again enriched with negative ions in order to reestablish its normal electrical conditions.

Figure 3:
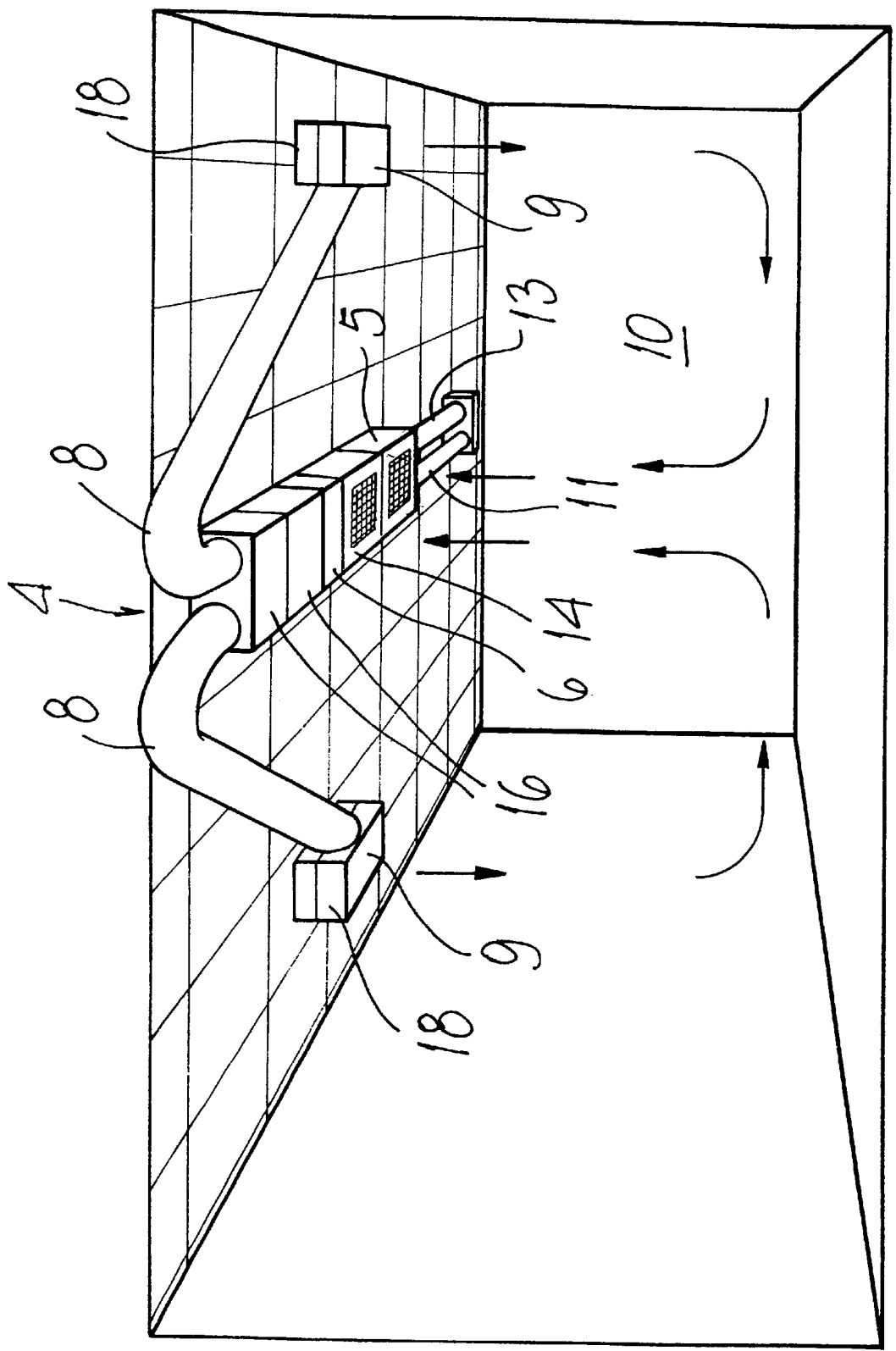
FIG. 3 is a view of an application of the device of the preceding figures.

With reference to the accompanying figures, the device for general sanitizing, generally designated by the reference numeral 4, is substantially constituted, along the direction in which the air stream flows, by a means 5 for aspirating the air to be sanitized, by a dust collection means 6, by an ionizing means 7 and by a conveyance means 8 for connection to a means 9 for distributing the sanitized air in an enclosed space 10. In detail, and particularly with reference to FIGS. 2 and 3, the aspirator means 5, of a per se known type, continuously aspirates fresh air through the duct 11 and simultaneously aspirates, by virtue of the grille 12, air from the space 10 and subsequently expels it through the duct 13. In this case, the aspirator means 5 is preset to aspirate fresh air and expel internal air with a 70/30 ratio. As an alternative, it is possible to adopt an aspirator means with full recycling or full aspiration according to the different requirements of the system. Downstream of the aspirator means 5 there is a known type of mixing unit 14, which combines the stream of fresh air with recycled air that arrives from the space 10 through the grille 15 so as to form the stream of air to be sanitized. This stream is in turn conveyed into the dust collection means 6, which is of a known type and is constituted by at least two stages, respectively for mechanical prefiltering and for filtering by electrostatic precipitation. In particular, the prefiltering stage includes a pair of filters, respectively made of acrylic fiber and metallic mesh, which trap the larger dust particles, indicatively with a diameter between 1 and 100 microns. Then the stage for filtration by electrostatic precipitation, through the electrification and trapping sections, stops the finer dust and accordingly the bacteria and microbes that accompany it. Downstream of the dust collection means 6 there are one or more per se known climate-control units 16, preset to give the dust-free air suitable temperature and humidity characteristics according to the requirements of the space 10 into which the air is released once it has been sanitized. At this point, a manifold distributes the dust-free and conditioned air into the various conveyance means 8. The ionizing means 7 is arranged within the conveyance means and consists of electrodes 17 which emit negative ions and are uniformly distributed along the conveyance means 8, in a central position with respect to the passage section and with their point directed in the direction in which the air flows. The electrodes 17 produce, around them, a strong negative ionizing field which is capable of saturating the conveyance means 8. This saturation is kept constant during the operation of the device 4 and performs a first action, which consists in preventing the forming of molds and bacterial colonies, and a second action, which consists in reducing to a physiological level the presence of bacteria, microbes, odors et cetera in the air that flows through. At the end of the conveyance means 8, proximate to the distribution means 9, there is the neutralizing means 18, which consists of a positively charged grid 19 which removes the excess negative ions of the flowing air so as to reestablish its correct electrostatic balance. Then, downstream of the neutralizing means 18, directly before the distribution means 9, there is a reviving means 20 which consists of further electrodes 21 which emit negative ions (not shown), like the preceding ones, and give the flowing air the electrical characteristics that are suitable for the space into which the air will be released. Finally, the distribution means 9 is formed by ordinary grilles 9.*a* or by diffusers 9.*b* which are flush with the surface of the ceiling and diffuse the sanitized air into the enclosed space. The device is furthermore provided with a programmable electronic controller 22 for supervision and monitoring, which appropriately drives the above described means.

Figure 4:
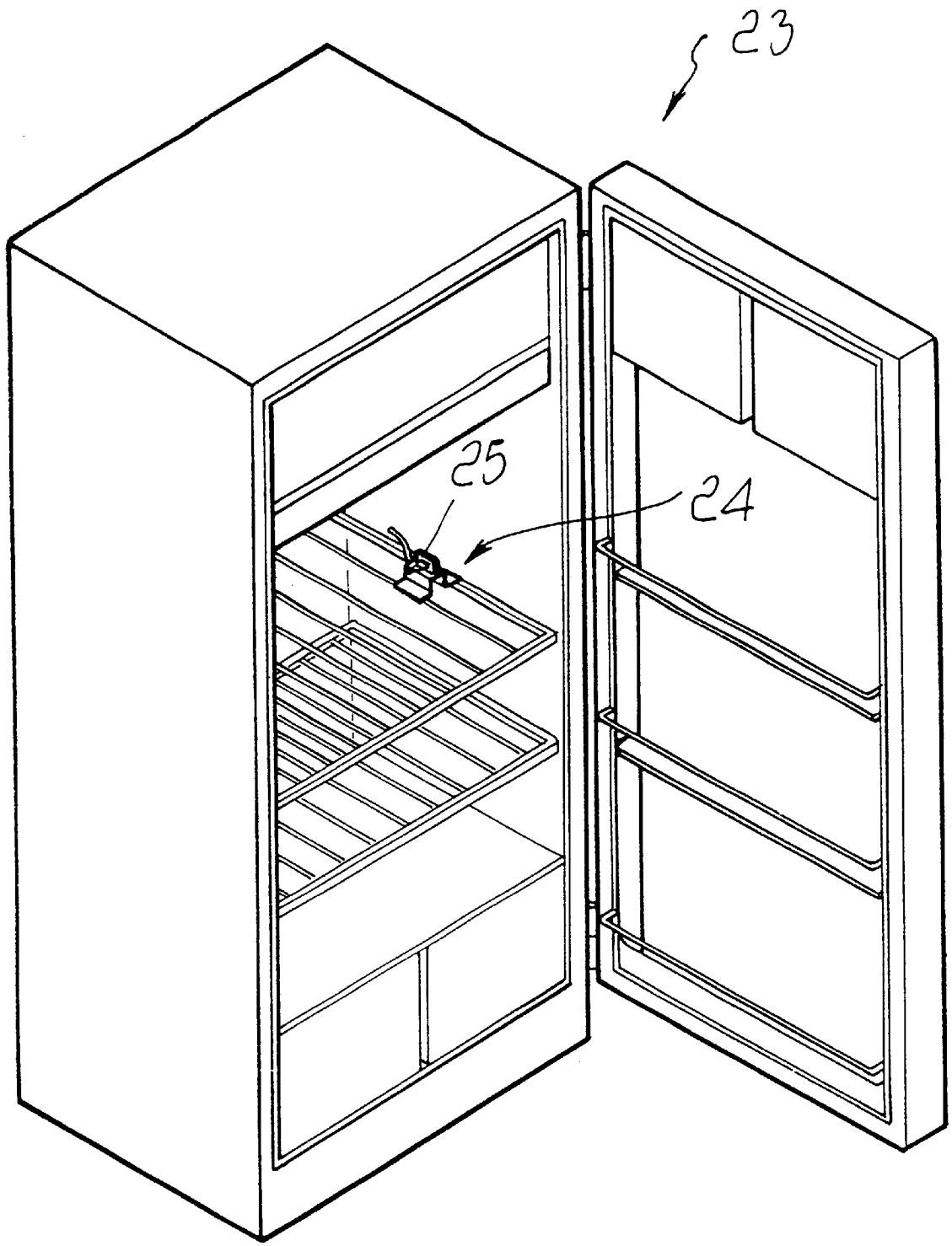
FIG. 4 is a perspective view of a refrigerator which includes an example of localized sanitizing device according to the invention.

The particularity of the method for the localized sanitizing of air and similar gas mixtures consists of the fact that it includes a continuous and constant or intermittent negative ionization of the air of an enclosed space without producing ozone, so as to perform a strong bactericidal and microbicidal action on the air. In particular, the concentration of negative ions per unit of air is at least two orders of magnitude higher than the concentration that is present in natural conditions, which in free air is approximately 400–1200 ions per cubic centimeter. The device that performs the method can find many applications. FIG. 4 illustrates, for example, a domestic refrigerator, generally designated by the reference numeral 23, whose walls delimit a volume of air to be treated by negative ionization. An ionizing means, generally designated by the reference numeral 24, is arranged inside the refrigerator 23 and is constituted by a pointed emitter electrode 25 which is directed into the cavity thus delimited. The electrode is connected, by virtue of conventional wired connections, to an electronic programming and monitoring controller (not shown) which is accommodated in the motor housing (not shown) on the rear or in an appropriately provided compartment arranged in the refrigerator 23. The Applicant has conducted several comparative tests, introducing in the refrigerator for example respectively cheese accurately wrapped in transparent film and unwrapped cheese, and noting that at the normal cooling temperature and with continuous and constant negative ionization the unwrapped cheese remains unchanged for over a month, while the wrapped cheese, after a few days, already shows the first signs of decay, which consist in the appearance of surface mold. The unwrapped cheese was then subjected to a tasting test, which showed that the taste and odor had not changed over time due to the preservation treatment it had undergone. The described method and device are also used in the preparation of food products and particularly in the production of fresh and dried pasta, as well as in the butchering of meat in general. In these cases, the individual ingredients and the product are subjected to different stages of preparation, and the respective containers are subjected to localized negative ionization treatments to be performed by virtue of suitable devices (not shown) which are equipped with an ionization means. Preferably, intermittent negative ionization is used when the wear of the emitter electrodes, if used continuously, may turn out to be excessive due to the intense electrical potential to which they are subjected. Furthermore, the first tests that have been conducted seem to show that negative ionization has a neutralizing effect on toxic gaseous compounds such as benzene, $NO_x$ and the like or, at least, an action which converts them into non-toxic gaseous compounds such as $CO_2$.

In practice it has been found that the method and the device thus described achieve the intended aim and objects, since in the case of generalized sanitizing, by virtue of the combination of a dust collection step and of an ionization step and correspondingly of dust collection and ionizing means, the treated air is given high purity characteristics. Furthermore, the device offers a high standard of safety, since in case of failure, for example of the neutralizing means, the controller acts instantly to stop the emission of negative ions. Finally, the device can be applied conveniently in seasoning rooms for example for cheeses, pork meat and in general in rooms for preservation of food products exposed to free air, since by drastically reducing the presence of bacteria and microbes one accordingly prevents the forming of molds on the surface of said products. In the case of localized sanitizing, it has been found in practice that the method and the device thus described achieve the intended aim and objects, since they allow the preparation and preservation in air, in almost ideal aseptic conditions, of easily perishable products and derivatives thereof, such as for example organic waste. In practice, this method allows to extend the life of a product and allows, in combination with the mentioned "external" and "internal" methods, respectively lower energy consumption and lower use of preservatives or the use of preservatives having a lower chemical impact. Finally, the application of the device is simple and inexpensive and can be performed with a small number of simple steps even in existing equipment.

The method and the device according to the invention are susceptible of numerous modifications and variations, all of which are within the scope of the same inventive concept expressed herein.

All the details may furthermore be replaced with other technically equivalent elements.

In practice, the materials used, as well as the contingent shapes and dimensions, may be any according to the requirements.

What is claimed is:

1. A method for the general and localized sanitizing of air and similar gas mixtures, comprising a negative ionization of the air of an enclosed environment, said negative ionization having a bactericidal and microbicidal action on said air and having a neutralizing action on toxic gaseous compounds or at least converting said compounds into non-toxic compounds, said method comprising an initial step for aspirating said air to be sanitized and a final step for releasing said sanitized air into an enclosed environment, said method further comprising intermediate steps of dust collection by electrostatic precipitation of said air to be sanitized, an ionizing step for effecting negative ionization of said dust-free air and at least one conditioning step for conditioning said air to be sanitized, said conditioning step being effective to provide said air with temperature and humidity characteristics which are suitable for said environment, said conditioning step being carried out between said dust collection step and said ionization step.

2. The method according to claim 1, comprising a neutralization step for neutralizing the excess negative ions by electrical neutralization, said neutralization step being carried out between said ionizing step and said releasing step.

3. The method according to claim 2, comprising at least one step for the electrostatic reviving of said sanitized air by emission of new concentrations of negative ions, said reviving step being carried out between said neutralization step and said release step.

4. The method according to claim 1, characterized in that said environment is enclosed.

5. A device for the general and localized sanitizing of air and similar gas mixtures to be sanitized in an enclosed environment, comprising:

means for ionizing said air to be sanitized without producing ozone, said means for ionizing comprising electrodes which emit negative ions;

aspirator means connected to said means for ionizing; and conveyance means connected to said means for ionizing, for conveying said air to be sanitized to distribution means for distributing sanitized air in said enclosed environment, said conveyance means comprising, in the direction of flow of said air to be sanitized, a means for collecting, by electrostatic precipitation, dust from said air to be sanitized to produce dust-free air and means for ionizing said dust-free air, wherein said aspirator means includes means for expelling air from inside said enclosed environment and simultaneously aspirating air from outside said enclosed environment, whereby said aspirator means is capable of mixing air from outside said environment with air from inside said environment.

6. The device according to claim 5 further comprising at least one mixing unit which combines said aspirated external air with internal air extracted from said environment, said mixing unit being provided downstream of said aspirator means and upstream of said dust collection means.

7. The device according to claim 6, wherein said dust collection means comprises at least one mechanical filter and at least one electrostatic precipitation filter.

8. The device according to claim 7, further comprising at least one conditioning unit which provides said dust-free air with temperature and humidity conditions which are suitable for said environment, said conditioning unit being arranged downstream of said dust collection means and upstream of said ionizing means.

9. The device according to claim 8, wherein said ionizing means comprises a plurality of electrodes which emit negative ions and are uniformly distributed along said conveyance means, in a central position with respect to the passage section, and are directed in the direction in which said dust-free air flows.

10. The device according to claim 9, further comprising a neutralizing means for neutralizing excess ions in said sanitized air which comprises at least one positively charged grid which, by affecting said sanitized air, provides for the electrical neutralization of said excess ions, said neutralizing means being provided downstream of said ionizing means proximate to said distribution means.

11. The device according to claim 10, further comprising a reviving means which includes at least one electrode which emits negative ions so as to give said sanitized air appropriate electrical characteristics, said reviving means being arranged downstream of said neutralizing means and directly upstream of said distribution means.

12. The device according to claim 5, characterized in that said electrodes which emit negative ions act on the air volume of said enclosed environment.

13. The device according to claim 5, further comprising an electronic controller which supervises said device.

14. A device for the general and localized sanitizing of air or similar gas mixtures to be sanitized in an enclosed environment, comprising:

a first ionizer comprising electrodes which emit negative ions, said ionizer ionizing said air or gas mixtures without producing ozone;

an aspirator connected at least indirectly to said ionizer; and a conveyor connected at least indirectly to said ionizer, for distributing sanitized air in said enclosed environment, said conveyor comprising a dust collector disposed along a flow path of said air to be sanitized and a second ionizer, said second ionizer ionizing said dust-free air, wherein said aspirator includes an outlet duct expelling air from inside said enclosed environment and simultaneously aspirating air from outside said environment, said aspirator including a mixer for mixing air from outside said environment with air from inside said environment.

* * * * *